(12) United States Patent
Velschow et al.

(10) Patent No.: US 11,041,491 B2
(45) Date of Patent: Jun. 22, 2021

(54) MICRO DOSAGE PERISTALTIC PUMP FOR MICRO DOSAGE OF FLUID

(71) Applicant: Fluisense ApS, Allerød (DK)

(72) Inventors: Sten Velschow, Vedbæk (DK); Martin Toft Madsen, København Ø (DK); Alistair David Morton, Kastrup (DK); Michael Hansen, Faaborg (DK)

(73) Assignee: FLUISENSE APS, Allerod (DK)

( * ) Notice: Subject to any disclaimer, the term of this patent is extended or adjusted under 35 U.S.C. 154(b) by 93 days.

(21) Appl. No.: 16/072,627

(22) PCT Filed: Jan. 24, 2017

(86) PCT No.: PCT/DK2017/050014
§ 371 (c)(1),
(2) Date: Jul. 25, 2018

(87) PCT Pub. No.: WO2017/129193
PCT Pub. Date: Aug. 3, 2017

(65) Prior Publication Data
US 2019/0032651 A1    Jan. 31, 2019

(30) Foreign Application Priority Data
Jan. 25, 2016    (DK) .......................... PA 2016 70037

(51) Int. Cl.
*F04B 43/12*    (2006.01)
*F04B 53/16*    (2006.01)
(Continued)

(52) U.S. Cl.
CPC ...... *F04B 43/1238* (2013.01); *F04B 43/1276* (2013.01); *F04B 53/16* (2013.01); *F04B 53/22* (2013.01); *A61M 5/14232* (2013.01)

(58) Field of Classification Search
CPC .. F04B 43/1238; F04B 43/1276; F04B 53/16; F04B 53/22; F04B 43/14232; A61M 5/14228; A61M 5/14248; A61M 5/14232
See application file for complete search history.

(56) References Cited

U.S. PATENT DOCUMENTS 1,741,070 A * 12/1929 Cornet y Oliveras ...................... F04B 43/1276 417/477.8
3,644,068 A *  2/1972 Lepak ................. F04B 43/1276 417/477.7

(Continued)

FOREIGN PATENT DOCUMENTS

CN       85204827 U    10/1986
CN       87107936 A     7/1988
(Continued)

*Primary Examiner* — Nathan C Zollinger
(74) *Attorney, Agent, or Firm* — Dinsmore & Shohl LLP

(57) ABSTRACT

The invention regards a micro dosage peristaltic pump (2) for micro dosage of a fluid, comprising: a housing (4) with an inner annular surface (5), wherein the annular surface comprises an opening (12), a flexible tube (6), wherein a section of the tube is placed upon the annular surface (5), a compression element (7) configured for peristaltic engagement with the section of the tube placed upon the annular surface (5), at least one counter acting element (11), an arm (10) comprising the compression element (7) and the counter acting element (11), wherein the arm (10) is rotatably mounted with a rotation axis perpendicular to the arm, driving means for rotating the arm (10), and thereby moving the compression element (7) and the counter acting element (11) in a circular motion.

27 Claims, 6 Drawing Sheets

(51) Int. Cl.
*F04B 53/22* (2006.01)
*A61M 5/142* (2006.01)

(56) References Cited

U.S. PATENT DOCUMENTS

| | | | | |
|---|---|---|---|---|
| 4,441,867 A * | 4/1984 | Berelson | ............ | F04B 43/1292 |
| | | | | 417/475 |
| 4,559,040 A | 12/1985 | Horres et al. | | |
| 4,702,679 A * | 10/1987 | Malbec | ............... | F04B 43/1253 |
| | | | | 417/475 |
| 5,326,236 A | 7/1994 | Kramer et al. | | |
| 9,140,251 B2 * | 9/2015 | Beiriger | .............. | F04B 43/1276 |
| 9,784,263 B2 * | 10/2017 | Hendricks | ........... | F04B 43/1253 |
| 9,874,207 B2 * | 1/2018 | Buckle | ................ | F04B 43/1253 |
| 2012/0282126 A1 * | 11/2012 | Brandt | ................. | F04B 43/082 |
| | | | | 417/477.9 |
| 2014/0003985 A1 * | 1/2014 | Schaefer | ................ | B65D 51/00 |
| | | | | 417/476 |
| 2014/0356202 A1 | 12/2014 | Sorensen et al. | | |
| 2017/0292510 A1 * | 10/2017 | Buckle | ................ | F04B 43/1253 |
| 2019/0062152 A1 * | 2/2019 | Xi | ........................... | C08L 75/04 |

FOREIGN PATENT DOCUMENTS

| | | | | | |
|---|---|---|---|---|---|
| DE | 1953369 | A1 | 7/1970 | | |
| EP | 1880669 | A1 | 1/2008 | | |
| EP | 2451499 | B1 | 8/2013 | | |
| EP | 2674177 | A1 | 12/2013 | | |
| FR | 2021524 | A1 * | 7/1970 | .......... | F04B 43/1276 |
| FR | 2021524 | A1 | 7/1970 | | |
| GB | 1445731 | A * | 8/1976 | ............ | F04B 43/123 |
| GB | 1445731 | A | 8/1976 | | |
| GB | 2230301 | A | 10/1990 | | |
| JP | 49-84704 | | 11/1947 | | |
| JP | 53-43787 | | 9/1951 | | |
| JP | 60-97386 | | 7/1960 | | |
| WO | 9415098 | A1 | 7/1994 | | |
| WO | 2014045047 | A1 | 3/2014 | | |
| WO | 2014064414 | A1 | 5/2014 | | |

* cited by examiner

MICRO DOSAGE PERISTALTIC PUMP FOR MICRO DOSAGE OF FLUID

This application is the U.S. national stage of PCT/DK2017/050014 filed Jan. 24, 2017, which claims priority of Denmark Patent Application PA 2016 70037 filed Jan. 25, 2016 of which is hereby incorporated by reference in its entirety.

FIELD OF INVENTION

The invention relates to a micro dosage peristaltic pump for micro dosage of a fluid.

BACKGROUND OF THE INVENTION

Peristaltic pumps are widely used for medical purposes, from large pumps used to pump large volumes of blood, to miniature peristaltic pumps to pump small dosages of blood or medicament.

For medical purposes it is essential to avoid contamination of a pumped fluid. It is therefore essential that the fluid is not exposed to the surroundings, and that the pump can be properly cleaned and sterilised, both before use and in storage, as well as after use and in-between uses, and/or that the parts in contact with the fluid can be easily replaced or disposed of after use.

Peristaltic pumps are particularly suitable for medical purposes. In a peristaltic pump, the fluid is conducted through the pump in a pliable tube, and no other parts of the pump are in contact with the fluid. Furthermore, the pliable tube is typically a silicone tube, which is easily sterilised by radiation sterilisation, such as gamma radiation.

The pliable tube of a peristaltic pump in operational configuration will be compressed at one or more sites, this is also denoted the peristaltic coupling. However, peristaltic pumps that are stored and sterilised in a configuration where the tube is compressed, suffer from two main disadvantages:

Firstly, there is a risk of permanent deformation of the pliable tube during storage, and thus short shelf life of the pump. A deformed tube, such as a partly occluded tube, will affect the precision and reliability of the pump, and may compromise the safety by increased risk of air bubbles and clogging of the fluid.

Secondly, there is a risk of fusing opposing surfaces of the compressed pliable tube together during radiation sterilisation. The issue is more pronounced for micro dosage pumps where the diameter of the tube is smaller.

To mitigate the risks, the peristaltic pump may be stored and sterilised in a non-operational configuration. For example, the tube may be sterilised and stored separately, and then assembled into the pump shortly before use.

Correspondingly, the pump may be partly disassembled during storage, and upon assembling the tube becomes compressed. U.S. Pat. No. 4,559,040 describes a peristaltic pump comprising an eccentric rotor, and a detachable part of a stator, which has a configuration where the tube is not compressed, when the detachable part is removed.

However, for a peristaltic pump to be simple and easy to use, it is advantageous that the parts of the pump can be stored and sterilised in an assembled configuration.

EP 2 674 177 discloses a peristaltic pump, where the transition from mechanically distressed or unstressed tube configuration to stressed tube, occur while the parts of the pump are assembled. The compression/decompression of the tube occur by the engagement and lateral displacement of a multiple of gears.

There is a need for peristaltic pumps for micro dosage with improved precision and reliability, such as reduced risk of flow irregularities, and with improved continuous flow rates. It is furthermore desirable to obtain pumps with a minimum requirement of power and maintenance, thus comprising a minimum number of parts, simple to use, maintain and sterilise, and where the parts in contact with the fluids are easily replaced or disposed.

SUMMARY OF THE INVENTION

A first aspect of the invention relates to a micro dosage peristaltic pump 2 for micro dosage of a fluid, comprising:
a housing 4 with an inner annular surface 5, wherein the annular surface comprises an opening 12,
a flexible tube 6, wherein a section of the tube is placed upon the annular surface 5,
a compression element 7 configured for peristaltic engagement with the section of the tube placed upon the annular surface 5,
at least one counter acting element 11,
an arm 10 comprising the compression element 7 and the counter acting element 11,
wherein the arm 10 is rotatably mounted with a rotation axis perpendicular to the arm,
driving means for rotating the arm 10, and thereby moving the compression element 7 and the counter acting element 11 in a circular motion.

A second aspect of the invention relates to a kit of parts comprising the pump according to the first aspect of the invention, and one or more micro dosage peristaltic pump(s), wherein the parts are optionally assembled to a handheld device.

A third aspect of the invention relates to the use of the pump according to the first aspect of the invention for pumping fluids such as blood, anticoagulants, and medicaments.

DESCRIPTION OF THE DRAWINGS

The invention will in the following be described in greater detail with reference to the accompanying drawings.

FIG. 4A shows an embodiment with fully assembled parts, FIG. 4B shows the selected components (compression element, tube, counter acting element).

FIG. 5A shows an embodiment with fully assembled parts, FIG. 5B shows the selected components (compression element, tube, counter acting element).

FIG. 6A shows an embodiment with fully assembled parts, FIG. 6B shows the selected components (compression element, tube, counter acting element).

DETAILED DESCRIPTION OF THE INVENTION

Figure 1:
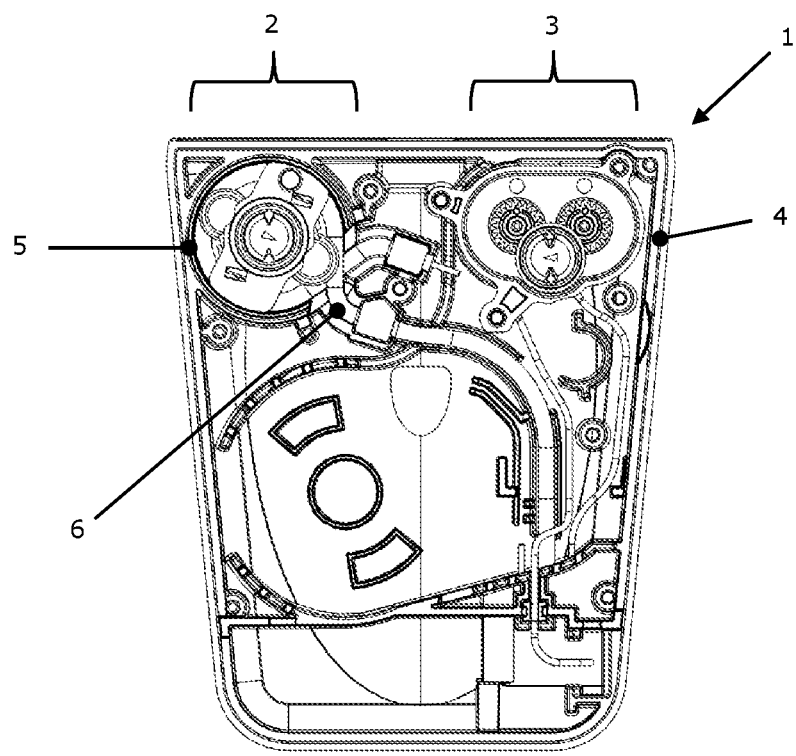
FIG. 1: shows a schematic top view of handheld medical device comprising an embodiment of the pump according to the present invention.

The present invention provides a micro dosage peristaltic pump with a shape and size allowing it to be built into a wearable or portable or handheld medical device 1 as illustrated in FIG. 1. The wearable device may comprise multiple micro dosage peristaltic pumps, where the different pumps may be applied for pumping different fluids. For example, the portable device 1 shown in FIG. 1, comprises two micro dosage pumps, where the first micro dosage pump 2 is according to the present invention, and may be used for pumping blood, and the second micro dosage pump 3 may of a different type, and may be used for pumping a medicament, such as an anticoagulant.

The housing may further comprise external holding elements for attaching the micro dosage peristaltic pump to a desired site.

By the term fluid as used herein is meant any substance that is capable of flow, such as liquids, gasses, plasmas, and plastic solids. Examples of fluids for peristaltic pumps for medical purposes may include blood and medicaments, such as anticoagulants.

Figure 2:
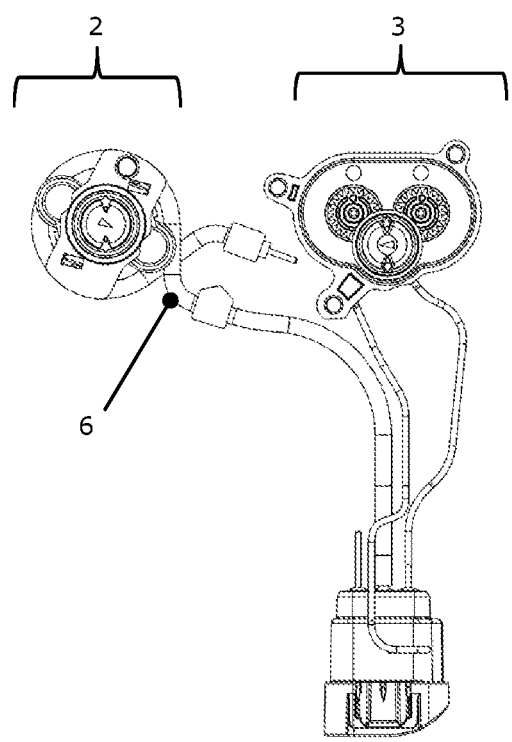
FIG. 2: shows a schematic top view of the device in FIG. 1 without the housing.

The pumps are placed inside a housing 4 that is part of the wearable device. FIG. 2 shows the pumps without the housing.

Figure 3:
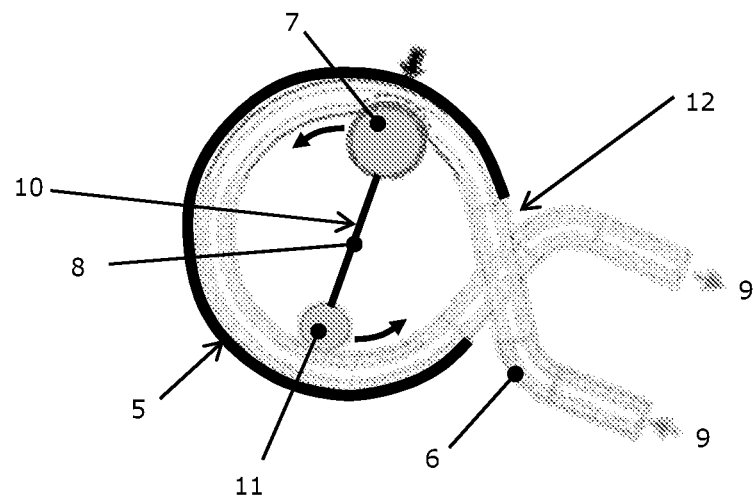
FIG. 3: shows a schematic top view of an embodiment of the micro dosage peristaltic pump according to the invention.

A sketch of the micro dosage peristaltic pump 2 according to the present invention is shown in FIG. 3.

The operational principle is based on a fluid being contained within a flexible tube 6, and where a section of the tube is placed upon an inner annular surface 5. The inner annular surface may be placed within the housing 4 as illustrated in FIG. 1.

A part of the flexible tube may be pinched closed, or occluded, by a compression element 7. The compression element squeezes the tube against the annular surface, such that the part of the tube under compression is pinched, fully or partly, closed, as indicated by an arrow in FIG. 3.

When the compression element is driven in a circular motion following along the annular surface, the fluid is being pumped by peristaltic motion. The circular motion is illustrated by arrows, where the circulation will occur around the rotation axis 8. During rotation, fluid is being pumped to and from the distal openings 9, as shown by arrows in FIG. 3.

The engagement between the compression element, the tube and the surface, is also denoted peristaltic engagement, or peristaltic coupling, and the process of peristaltic propulsion of the fluid in the tube is also known as peristalsis, and peristaltic motion.

The rotation of the compression element may be obtained by a rotatably mounted arm 10 comprising the compression element. This implies that the rotation axis will be perpendicular to the arm. The rotation axis may further be placed centrally to the arm.

To improve the mechanical stability of the arm, the arm may comprise a counter acting element 11 as shown in FIG. 3. The counter acting element may be placed at the opposite end of the arm to the compression element. Thus, as the arm is rotated around a rotation axis, the compression element and the counter acting element are driven in the same circular motion, but displaced in the revolution.

The counter acting element is stabilizing the rotation of the arm by engaging, or compressing, directly against the annular surface. Thus, the compression force of the compression element 7 against the tube placed upon the annular surface, is counter acted by the compression force of the counter acting element against the annular surface.

Figure 7:
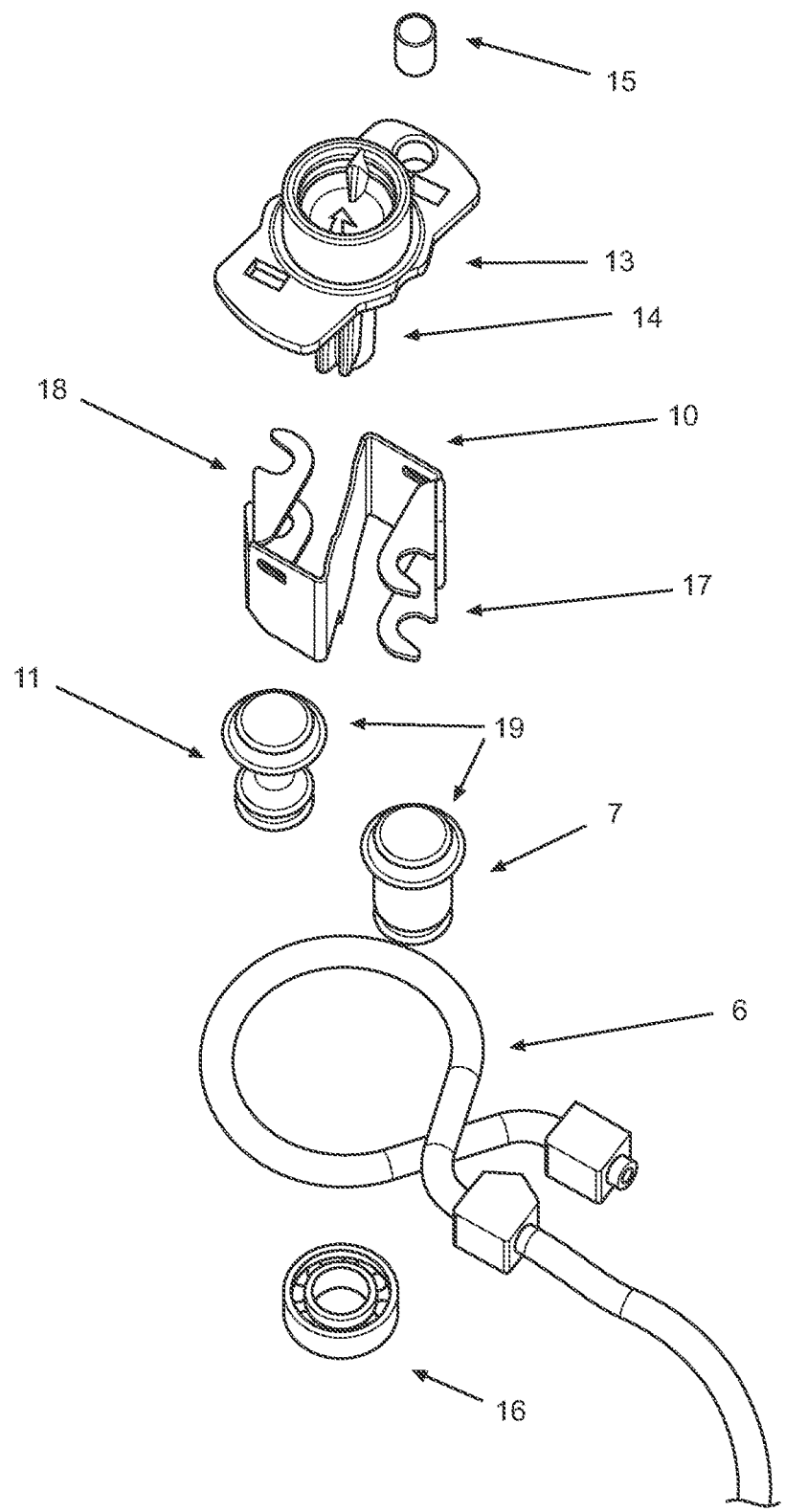
FIG. 7: shows an embodiment of a pump with a Z-shape flexible arm in exploded view.

The counter acting element 11 is configured to engage directly with the annular surface, without squeezing the tube against the annular surface. This may be obtained by the counter acting element comprising a tube receiving part, such as the counter acting element having a reel shape, as shown in FIG. 7.

In contrast to the counter acting element 11, the compression element 7 is squeezing the tube against the annular surface, and does not comprise a tube receiving part. Thus, the compression element may have the shape of a roller or a cylinder, as shown in FIG. 7.

The annular surface 3 of the invention has an opening 12. The flexible tube enters and exits through the opening, and the section of the tube within the annular part, is placed upon the inner annular surface.

Configurations

Figure 4:
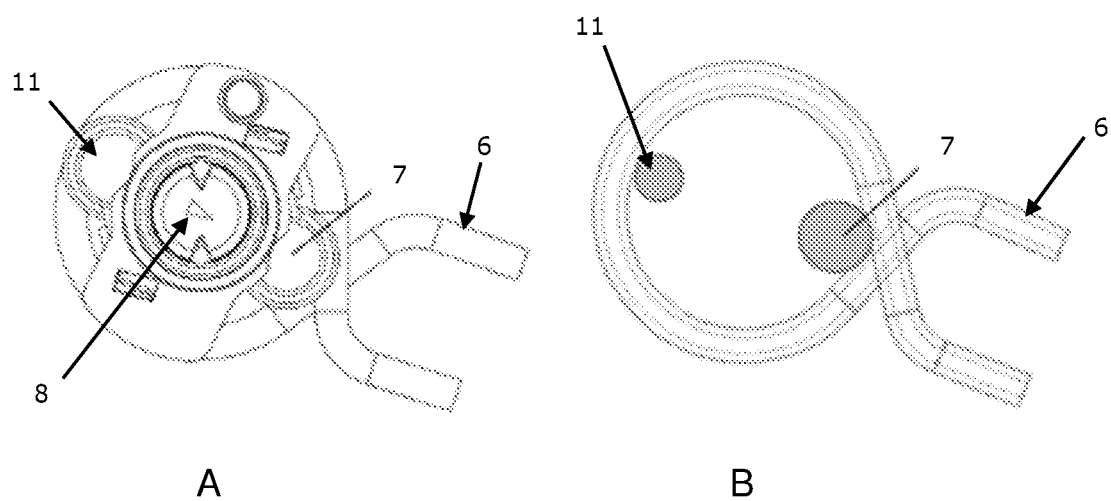
FIG. 4: shows a schematic top view of an embodiment of the pump in the parking position.

When the compression element 7 is facing the opening 12, the tube is not pinched and occluded, due to the absence of annular surface against which the tube can be squeezed. This position of the compression element is also called the dead point. Thus, in this configuration, the tube will be mechanically unstressed. The configuration is illustrated in FIG. 4. FIG. 4A shows an embodiment with fully assembled parts, and FIG. 4B shows the selected components (compression element, tube, counter acting element).

In the mechanically unstressed configuration, no parts of the tube is pinched, and the tube is fully open for a flow. The configuration is also referred to as the starting or parking position, the parking mode, or the mechanically unstressed mode. Upon continuous rotation of the compression element, the compression element will pass the parking position, or the dead point, at each revolution.

A micro dosage peristaltic pump, which has a parking position while the pump being in fully assembled and operational state, is especially advantageous for medical purposes. The sterilisation of a peristaltic pump and the flexible tube is preferably done by radiation sterilisation when the pump is in a configuration where the tube is not compressed. This avoids a risk of fusing, and partially/fully occluding, the tube during irradiation sterilisation. Thus, a micro dosage pump with a parking position can be sterilised at any time before storage or use, without further assembling needed after the sterilisation.

Figure 5:
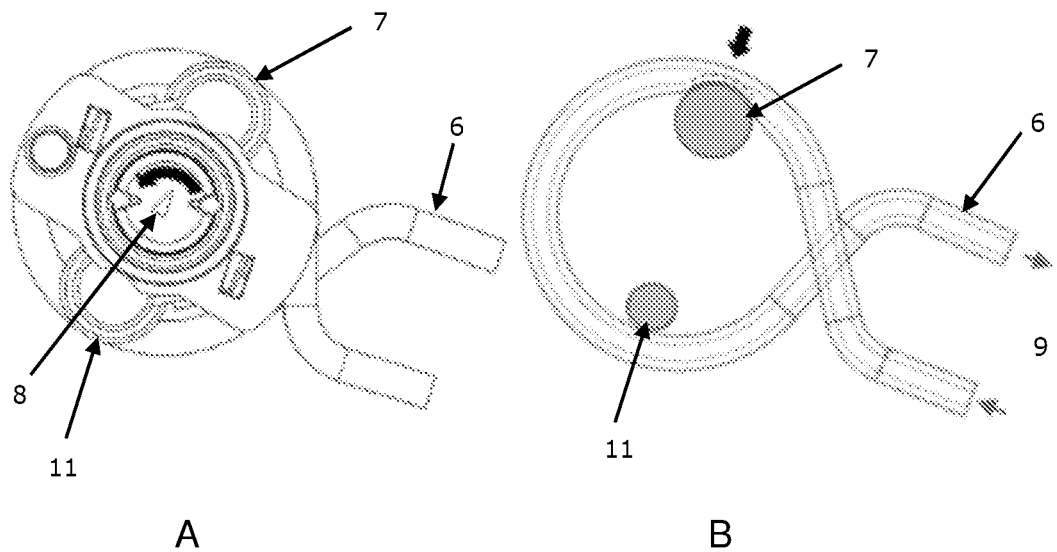
FIG. 5: shows a schematic top view of an embodiment of the pump, where the compression element has been rotated a central angle of ca. 90 degrees counterclockwise from the parking position.
Figure 6:
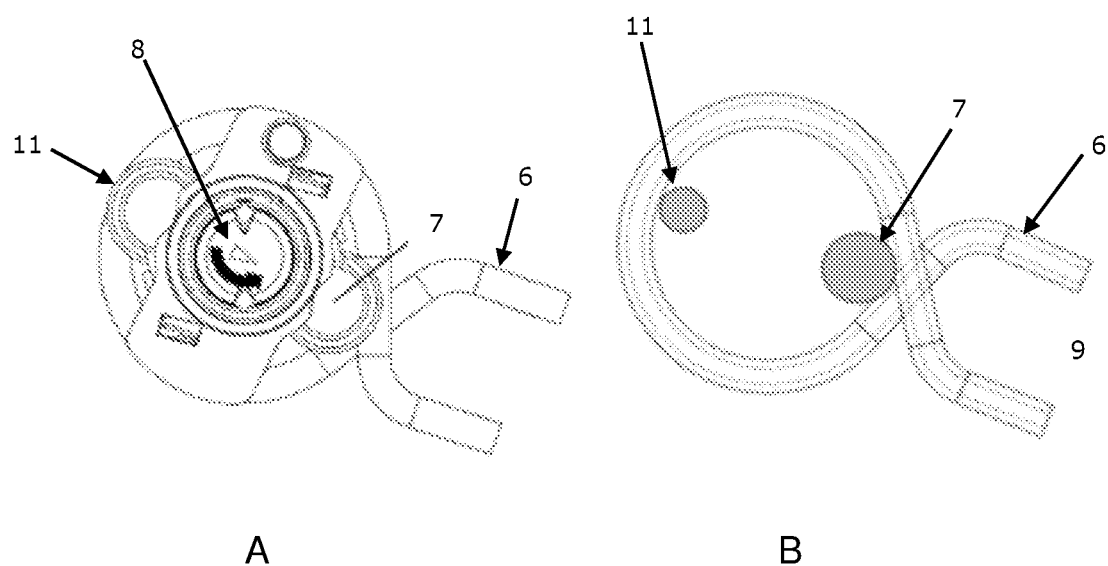
FIG. 6: shows a schematic top view of an embodiment of the pump, where the compression element has been rotated a central angle of 360 degrees counterclockwise from the parking position.

The configurations of the pump after sterilisation and in continuous operation are illustrated in FIGS. 5-6. Corresponding to FIG. 4, Figures A shows embodiments with fully assembled parts, and Figures B shows the selected components (compression element, tube, counter acting element).

The pump starts to pump fluid to and from the distal opening 9, when the compression element is rotated out of the dead point, and starts to pinch and occlude the tube as shown in FIG. 5. In FIG. 5, the compression element has been rotated a central angle of ca. 90 degrees counterclockwise from the parking position.

By the term "central angle" is meant the angle whose apex is the center of the circular rotation of the compression element, and whose legs are the radii intersecting the circle.

The central angle also corresponds to the degree of rotation of the arm 10 as shown in FIG. 3.

Upon each revolution of the compression element, i.e. for each 360 degree rotation from the parking position, the compression element will pass the dead point, as shown in FIG. 7. At this point, there will be a stop in the flow of the pumped fluid to and from the distal opening. During continuous operation, the stop in flow will be brief, and as the compression element rotates out of the dead point, fluid pumping is resumed as in the configuration shown in FIG. 6.

The pump dosing, or sampling, per revolution is determined by the point on the circumference of the annular surface, where the compression element engages with the tube and surface. However, variations in the point where the compression element start to engage with the tube may occur, and this will affect the precision and reproducibility of the sampling. In order to achieve maximum precision, any dosing over the dead-point must be avoided.

It is possible to start dosing from the same spot on the circumference by including means for measuring the position of the compression element or roller, This will result in a high reproducibility of the sampling.

Examples of means for measuring the position of a compression element include optical sensors, magnet/Hall sensors, electrical contacts, torque-based feedback, or means for accurately counting and controlling every step of the drive means.

In addition to measuring the position of the compression element, the position of the compression element may be controlled, and the control may be implemented in a computer.

Tubing

By the term flexible tube 6 as used herein is meant any hollow tube that is capable of being pinched closed by compression, and afterwards return to its original shape when not being pinched anymore. A hollow tube is further characterised by having a lumen surrounded by the tube wall.

For medical purposes the material of the tube should be capable of being cleaned, flushed and/or sterilized, and the tube material should not be reactive with fluids such as blood and medicaments. Examples of flexible tubes for peristaltic pumps for medical purposes include tubes of any type of silicone.

In general the tubing in peristaltic pumps must be compressed to less than the sum of the thickness of the two walls being compressed, to ensure complete closure of the lumen. Complete closure is essential for precise dosage of the pumped fluid upon each rotation of the compression element. Thus, the tube may be compressed to more than the sum of the two walls, such as at most 80 to 85% of the sum of the two walls.

The thicker the walls of the tubing the more energy is expended in occluding the lumen. Thus, if the flexible tube comprises a thin walled tube, the pump requires a minimum of energy to compress the tubing, and to ensure complete closure of the lumen for precise dosage of the fluid within.

Furthermore, if the inner diameter of the tube wall is small, less energy is expended in occluding the lumen. Flexible tubes with small inner diameters further enables precise and accurate dosage of even small micro liter doses, or micro liter flows.

Thus, a micro dosage pump as described in the current invention, can be used in a wearable system with limited battery power supply. The pump can further accurately deliver an exact flow or volume of fluid, by using tubing with small inner diameter.

Annular Surface

The annular surface 5 may be placed within a housing as shown in FIG. 1.

The annular surface upon which the section of the tube is placed, has an inlet and exit opening for the tube to enter. At the opening the tube may lie double, i.e. one tube section above the other, as exemplified in FIGS. 3-6.

The size of the opening will determine the time it takes the compression element to pass the dead point. If the opening is large, i.e. the central angle of the opening is large, the compression element will face the opening at more positions during a rotation, and as the pump will be in parking position as the compression element faces the opening, the tube will be mechanically unstressed for a longer time. If the opening is small, there may be only one position during rotation, wherein the compression element faces the opening, and thus the tube will be mechanically unstressed for a short time.

In an embodiment of the invention, the opening 12 has a central angle between 30-150°, more preferably between 55-125°, and most preferably between 80-100°. In another embodiment, the flexible tube 6 enters and exits the annular surface 5 through the opening 12. In another embodiment, the pump is configured such that the compression element 7 is not engaging with sections of the tube placed outside the annular surface 5. In a further embodiment, the pump is configured such that the compression element 7 is not peristaltically engaged to the tube 6, when the compression element is facing the opening 12.

The annular surface may further comprise extending guide elements (not shown) for retaining the flexible tube in position in relation to the annular surface. The guide elements may comprise a recess for receiving the flexible tube in order to hold the flexible tube in correct position. For example the recess or similar means may help prevent that the flexible tube is squired up or down by the motion of the compression means.

In an embodiment of the invention, the annular surface 5 comprises a recess for receiving the flexible tube 6.

Compression Element

The compression element 7 may be in the form of a roller, which have a cylindric shape. The cylindric surface of the roller can compress a tube evenly against a surface. Other examples of compression elements include "shoes", "wipers", "lobes", and "caps".

In an embodiment of the invention, the compression element 7 is a roller.

Pumps comprising multiple compression elements will inherently have variations in the flow rate during a 360 degrees rotation, due to the multiple compression elements. For example, a pump comprising two compression elements may have two different flow rates per 360 degrees rotation.

A pump with a single compression element facilitates the largest volume pumped with the same continuous flow rate, as the volume pumped with continuous flow rate is defined by a single rotation of the compression element. The longer continuous flow rate enables a more precise dosage and pump.

Furthermore, a pump with a single compression element results in fewer deformations of the tube during each 360 degrees rotation, or pumping cycle. Thus, the wear of the tubing and pump is reduced, and the energy consumption of the pump improved.

Wear of the tubing may include risk of spallation of the inner tubing wall, causing tubing materials to enter the blood stream of the patient.

Counter Acting Element

The purpose of the at least one counter acting element 11 is to counterbalance the compression element, and thus make the system more mechanically stable.

The counter acting element provides a counter force to the pressure of the compression element against the tube and annular surface, and thus ensures that the rotation driving means are subject to more balanced forces and remains centred.

The counter acting element is configured to have a tube receiving part, such that the counter acting element is not compressing the tube, when the counter acting element is pressed against the annular surface.

The counter acting element may have a reel shape or bobbin shape, and the bobbin can thus be pressed or rolled against the annular surface without compressing the tube.

In an embodiment of the invention, the at least one counter acting element 11 is configured for engaging with the annular surface 5, and essentially not engaging with the tube 6. In a further embodiment, the at least one counter acting element 11 has a reel or a bobbin shape. In another embodiment, the pump is configured such that the force of the engaging compression element 7 against the tube, is essentially equal to the force of the at least one counter acting element 11 against the annular surface 5.

Both the compression element (roller) and the counter acting element (bobbin) may comprise means for guiding the flexible tube. The means may for example be collars 19 on one or both ends of the bobbin and/or roller, as exemplified in FIG. 7.

Arm

The circular motion of the compression element and the counter acting element may be obtained by a rotatably mounted arm 10 comprising the elements, and where the rotatably mounted arm has a rotation axis perpendicular and centrally to the arm. When the arm is rotated around the rotation axis, the compression element is driven in a circular motion against the flexible tube, and the counter acting element is driven in a circular motion against the annular surface.

Better mechanical stability of the system (arm, compression element, and counter acting element) is obtained when the rotation axis is placed in the middle between the first and second end of the arm, and if the arm is rotation symmetric around the rotation axis. Furthermore it is advantageous for the stability, if the compression element and the counter acting element is placed at opposite ends of the arm, and displaced 180 degrees during their circular motion.

The rotation of the arm may be obtained by driving means, where the arm is not fixed with respect to the axis of the driving means.

In an embodiment of the invention, the arm 10 is rotation symmetric around the rotation axis. In another embodiment, the rotation axis 8 is placed in the middle between the first and second end of the arm 10. In another embodiment, the compression element 7 is placed at the first end of the arm, and the at least one counter acting element 11 is placed at the second end of the arm. In a further embodiment, the circular motion of the compression element 7 and the counter acting element 11 is displaced by 180°.

Tolerance Absorbing Means

Controlled compression and occlusion of the tubing is essential for the precision of the pump. If the degree of compression on the tube is not consistent, the degree of occlusion of the tube can vary, which may result in irregularities in the flow, as well as risk of back flow.

As described earlier, one way to ensure that the tube is fully occluded is to compress the tube to less than the sum of the two tube walls. However, to fully control the compression and occlusion, irregularities in the tube properties and irregularities in the annular surface must be taken into account as well.

The compression may be controlled by use of tolerance absorbing means incorporated into the system comprising compression element, arm, and counter acting element. The tolerance absorbing means reduce the variations in the compression force on the tube that are due to variations in the tube properties, such as diameter, thickness of tube walls or flexibility, and variations in the roughness of the annular surface engaging with the tube.

Examples of tolerance absorbing means include arms comprising flexible materials, such as flexible sheet materials, and compression elements being attached to the arm by receiving members with feather properties.

The ability to compensate for structural irregularities is particularly necessary in small pumps, where even small irregularities are relatively large, and where the tube walls are thin and/or the inner lumen of the tube is small.

For the dimensioning of the pump, it is advantageous that the tolerance absorbing means are placed on the concave side of the annular surface. Incorporating the absorbing means on the inside of the tube path allows for a smaller overall size of the pump relative to the volume pumped per pump revolution, i.e. the largest sample that can be dosed precisely and accurately by not dosing across the dead point can be incorporated inside a smaller pump size.

Additionally, the introduction of tolerance absorbing means allows for larger tolerance variations in the production, which means that the production of the various parts, such as tube, roller, and bobbin, may be less costly and less complex.

In an embodiment of the invention, the arm 10 and/or the receiving members 17, 18 are configured to be flexible. In another embodiment, the arm 10 and/or the receiving members 17, 18 are configured to be flexible in the direction parallel to the rotation plane.

In an embodiment of the invention, the arm 10 and/or the receiving members 17, 18 are placed on the concave side of the annular surface 5.

Assembly

FIG. 7 shows an embodiment of a pump in exploded view. In this embodiment, the arm 10 has a Z-shape. By the term "Z-shape" is meant a structure comprising three planar parts, where the two planar parts are parallel and spaced apart, and the third planar part is placed in between and connecting the two planar parts at a non-perpendicular angle.

In an embodiment of the invention, the arm 10 is a Z-shaped element.

The drive means 13 may comprise a shaft 14 that is rotatably around the longitudinal axis of the shaft, and the Z-shape may be engaged to a shaft, and thereby rotatably mounted. The shaft may comprise a central groove for receiving part of the arm, such as the central planar part of the Z-shape, as shown in FIG. 7.

The drive means may further comprise a magnet 15, and one or more bearings, such as a ball bearing 16.

The compression element 7 and the counter acting element 11 may be placed at opposite ends of the arm 10, as shown in FIG. 7. The compression element may be a roller, and the counter acting element a bobbin. When the drive means rotate the shaft, the Z-shaped arm rotate, and the roller and bobbin are driven in a circular motion. The roller is driven against the the tube and annular surface (not shown in FIG. 7), thereby compressing the flexible tube in a peristaltic motion, and the bobbin is driven against the annular surface.

For positioning the compression and counter acting element, the arm may comprise a first receiving member 17 at the first end of the arm, and a second receiving member 18 at the other end of the arm. The compression element and counter acting element may further comprise collars 19 for easy and stable engagement with the receiving members. The receiving members may further be configured to allow the roller and bobbin to rotate around their respective longitudinal axis.

In an embodiment of the invention, the arm 10 comprises a first receiving member 17 at the first end of the arm, and a second receiving member 18 at the second end of the arm. In a further embodiment, the first 17 and the second receiving members 18 are identical. In a further embodiment, the first receiving member 17 is configured to receive the compression element, and the second receiving member 18 is configured to receive the at least one counter acting element. In another embodiment, the receiving members 17, 18 are configured to detachably attach the compression element and the at least one counter acting element. In another embodiment, the receiving members 17, 18 are configured to allow the compression element and the counter acting element to rotate around their respective longitudinal axis.

The tolerance absorbing means in the assembly embodied in FIG. 7, may include the arm and/or the receiving members. The Z-shaped arm may comprise a flexible sheet material, and the Z-shape will thus be flexible along the planar parts, and/or in the bends between the planar parts. Furthermore, the receiving members may be flexible relative to the planar parts of the arm.

In an embodiment of the invention, the arm 10 is made of a flexible sheet material. In another embodiment of the invention, the receiving members 17, 18 are flexibly relative to the arm.

The Z-shaped flexible arm, and/or the flexible receiving members, ensure that any variations or roughness of the components are compensated for in a simple but highly effective manner. Thus, by using the Z-shaped flexible arm it is possible to precisely dose or dispense even very small volumes of a fluid, and surprisingly high precision of micro dosage peristaltic pumps can be obtained.

In an embodiment of the invention, the pump is configured to provide a dose equal to or below 50.0 μL, more preferably equal to or below 25.0 μL, and most preferably equal to or below 10.0 μL. In a further embodiment, the pump is configured to provide a dosage precision, measured as the relative standard deviation (RSD), of at least ±5% RSD, more preferably ±2% RSD, and most preferably ±1% RSD.

Figure 8:
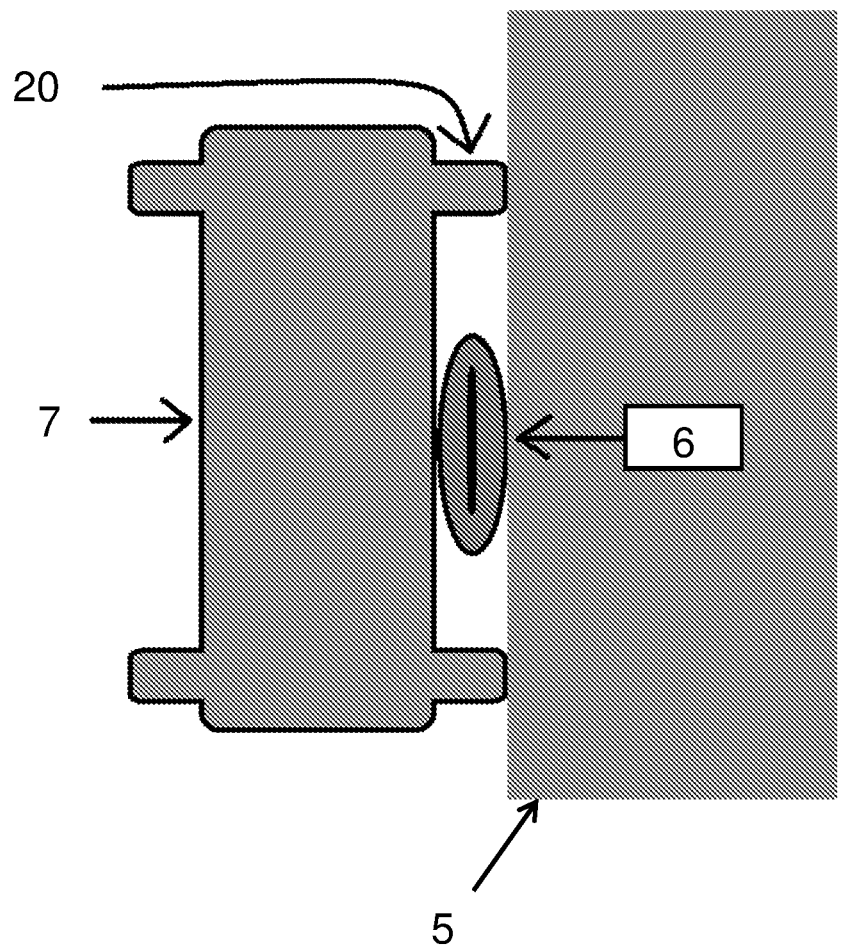
FIG. 8: shows a schematic cross-section of an embodiment of a compression element occluding a flexible tube, where the compression element comprises lips configured to restrict the maximum occlusion of the flexible tube.

The assembly including the tolerance absorbing means facilitates an even pressure on the flexible tube during operation taking account of irregularities such as surface roughness. However, for optimal occlusion and the long-term durability of the flexible tube, the tube should not be compressed to more than 80 to 85% of the sum of the two walls thickness. Thus, to ensure a limit to the maximum pressure on the flexible tube, the compression element may further comprise one or more protruding elements, such as a lip. FIG. 8 shows an embodiment of a compression element 7 comprising two lips 20, where a lip is a protruding element configured to restrict the maximum pressure or occlusion of the flexible tube. The lip may have a shape similar to a collar. The lips provide a steric obstacle, restricting the maximum occlusion of the flexible tube. Thus, irrespective of the softness of the flexible tube, or strength of the tolerance absorbing means, the flexible tube cannot be compressed more than defined by the protruding element.

In an embodiment of the invention, the compression element further comprises one or more protruding element(s) 20 configured to restrict the maximum occlusion of the flexible tube.

REFERENCE NUMBERS

1—wearable device
2—first micro dosage pump
3—second micro dosage pump
4—housing
5—annular surface
6—flexible tube
7—compression element
8—rotation axis
9—distal opening
10—arm
11—counter acting element
12—opening
13—driving means
14—shaft
15—magnet
16—bearing
17—first receiving member
18—second receiving member
19—collar
20—protruding lip element

The invention claimed is:
1. A micro dosage peristaltic pump for micro dosage of a fluid, comprising:
  a housing with an inner annular surface, wherein the annular surface comprises an opening;
  a flexible tube, wherein a section of the tube is placed upon the annular surface;
  a compression element configured for peristaltic engagement with the section of the tube placed upon the annular surface;
  at least one counter acting element configured for engaging with the annular surface, and essentially not compressing the tube;
  an arm having a first end and an opposing second end, the arm comprising the compression element and the at least one counter acting element, the arm being rotatably mounted with a rotation axis perpendicular to the arm, wherein the compression element is placed at the first end of the arm, the flexible tube being compressed at the first end of the arm when the compression element faces the inner annular surface and the flexible tube not being compressed at the second end of the arm when the at least one counter acting element faces the inner annular surface, wherein a straight line can be defined from the compression element to the at least one counter acting element passing through the rotation axis; and
  driving means for rotating the arm, and thereby moving the compression element and the at least one counter acting element in a circular motion, wherein the tube is unstressed when the compression element is facing the opening.

2. The pump according to claim 1, wherein the annular surface comprises a recess for receiving the flexible tube.

3. The pump according to claim 1, wherein the opening has a central angle between 30-150°.

4. The pump according to claim 1, wherein the flexible tube enters and exits the annular surface through the opening.

5. The pump according to claim 1, configured such that the compression element does not engage with sections of the tube placed outside the annular surface.

6. The pump according to claim 1, configured such that the compression element is not peristaltically engaged to the tube, when the compression element is facing the opening.

7. The pump according to claim 1, wherein the compression element is a roller.

8. The pump according to claim 1, wherein the compression element further comprises one or more protruding element(s) configured to restrict the maximum occlusion of the flexible tube.

9. The pump according to claim 1, wherein the at least one counter acting element has a reel or a bobbin shape.

10. The pump according to claim 1, configured such that the force of the compression element against the tube is essentially equal to the force of the at least one counter acting element against the annular surface.

11. The pump according to claim 1, wherein the arm is rotation symmetric around the rotation axis.

12. The pump according to claim 1, wherein the rotation axis is placed in the middle between the first and second end of the arm.

13. The pump according to claim 1, wherein the arm is a Z-shaped element.

14. The pump according to claim 1, wherein the circular motion of the compression element and the at least one counter acting element is displaced by 180°.

15. The pump according to claim 1, wherein the arm comprises a first receiving member at the first end of the arm, and a second receiving member at the second end of the arm.

16. The pump according to claim 15, wherein the first and the second receiving members are identical.

17. The pump according to claim 15, wherein the first receiving member is configured to receive the compression element, and the second receiving member is configured to receive the at least one counter acting element.

18. The pump according to claim 15, wherein the receiving members are configured to detachably attach the compression element and the at least one counter acting element.

19. The pump according to claim 15, wherein the receiving members are configured to allow the compression element and the at least one counter acting element to rotate around their respective longitudinal axis.

20. The pump according to claim 15, wherein the arm and/or the receiving members are configured to be flexible.

21. The pump according to claim 15, wherein the arm and/or the receiving members are configured to be flexible in the direction parallel to a rotation plane.

22. The pump according to claim 15, wherein the arm and/or the receiving members are placed on a concave side of the annular surface.

23. The pump according to claim 1, wherein the arm is made of a flexible sheet material.

24. The pump according to claim 15, wherein the receiving members are flexible relative to the arm.

25. The pump according to claim 1, configured to provide a dose equal to or below 50.0 µL.

26. A kit of parts comprising the pump according to claim 1, and one or more micro dosage peristaltic pump(s).

27. The pump according to claim 1, wherein the compression element is a single compression element and the at least one counter acting element is a single counter acting element, the elongated arm consisting of the single compression element and the single counter acting element.

* * * * *